(12) United States Patent
Grygier et al.

(10) Patent No.: US 7,719,675 B2
(45) Date of Patent: May 18, 2010

(54) METHOD FOR OPTICAL CHARACTERIZATION AND EVALUATION OF OPTICALLY VARIABLE DEVICES AND MEDIA

(75) Inventors: Robert K. Grygier, Newark, DE (US); Kelan Wieloch, Boothwyn, PA (US)

(73) Assignee: Applied Extrusion Technologies, Inc., New Castle, DE (US)

( * ) Notice: Subject to any disclaimer, the term of this patent is extended or adjusted under 35 U.S.C. 154(b) by 630 days.

(21) Appl. No.: 11/678,918

(22) Filed: Feb. 26, 2007

(65) Prior Publication Data

US 2007/0201039 A1 Aug. 30, 2007

Related U.S. Application Data

(60) Provisional application No. 60/777,486, filed on Feb. 28, 2006.

(51) Int. Cl.
*G01J 3/00* (2006.01)
*G01N 21/17* (2006.01)
(52) U.S. Cl. .................. 356/300; 356/326; 356/328
(58) Field of Classification Search .............. 356/73
See application file for complete search history.

(56) References Cited

U.S. PATENT DOCUMENTS

| | | | |
|---|---|---|---|
| 5,032,003 A | 7/1991 | Antes | |
| 5,737,125 A | 4/1998 | Ohashi | |
| 5,781,316 A | 7/1998 | Strahl et al. | |
| 2004/0101982 A1 | 5/2004 | Woontner | |
| 2004/0202942 A1* | 10/2004 | Takeyama | 430/1 |
| 2005/0112472 A1 | 5/2005 | Kutsch et al. | |

FOREIGN PATENT DOCUMENTS

| | | | |
|---|---|---|---|
| JP | 60-162930 | * | 8/1985 |
| JP | 04145341 | | 5/1992 |
| JP | 06-66679 | * | 3/1994 |
| JP | 09196813 | | 7/1997 |

OTHER PUBLICATIONS

Lemelin G et al: "Holographic imaging of 3D objects on dichromated polymer systems" Pure Appl. Opt., vol. 5, 1996, pp. 95-103, XP020070742.
Litvinenko A S et al: "The device of measurement of parameters of holograms" Laser and Fiber-Optical Networks Modeling, 2004. Proceedings of LFNM 2004. 6th International Conference on Kharkov, Ukraine Sep. 6-9, 2004, Piscataway, NJ, USA, IEEE, Sep. 6, 2004, pp. 302-304, XP010760976, ISBN: 0-7801-8429-6—figure 1.
International Search Report for PCT/US2007/062853 mailed Sep. 3, 2007.

* cited by examiner

*Primary Examiner*—F. L Evans
(74) *Attorney, Agent, or Firm*—Caesar, Rivise, Bernstein, Cohen & Pokotilow, Ltd.

(57) ABSTRACT

Methods for evaluating an optically variable device ("OVD") or optically variable media ("OVM") are disclosed. The methods include the steps of applying light of a single wavelength from a calibrated light source to the OVD or OVM; measuring the light diffracted by the OVD or OVM with an integrating sphere; measuring the total incident light on the OVD or OVM; and calculating a diffraction efficiency for the OVD or OVM at the single wavelength based on the measurement of light diffracted and the measurement of total incident light.

29 Claims, 7 Drawing Sheets

METHOD FOR OPTICAL CHARACTERIZATION AND EVALUATION OF OPTICALLY VARIABLE DEVICES AND MEDIA

CROSS-REFERENCE TO RELATED APPLICATIONS

This utility application claims the benefit under 35 U.S.C. §119(e) of Provisional Application Ser. No. 60/777,486 filed on Feb. 28, 2006 entitled OPTICAL METHOD FOR THE CHARACTERIZATION, EVALUATION AND PRODUCTION OF OPTICALLY VARIABLE DEVICES OR MEDIA, the entire disclosure of which is incorporated by reference herein.

FIELD OF THE INVENTION

The disclosure relates to the field of holographic films, surface relief gratings, optically variable devices or optically variable media. More specifically, the disclosure relates to the measurement of the optical properties of these devices and media and the use of these measurements to evaluate, rank or specify the optical quality, optical characteristics, or the visual appearance of these materials.

BACKGROUND OF THE INVENTION

Optically variable devices ("OVD") are optical devices, which diffract, refract, transmit, absorb, or scatter light and whose optical properties can vary within that device. Some examples of OVD would be holographic films, holograms, including: reflection holograms, absorption holograms and polarization holograms, diffraction gratings, embossed films, original artwork, embossing rolls, and replicas. Optically variable media ("OVM") are optical media, which diffract, refract, transmit, absorb, or scatter light and whose optical properties can vary within that device. Some examples of OVM which can be used to make OVD would be polymers, polymer films, multilayer films, films with inclusions, films with embossing layers, photoresist, epoxies, silicones, lacquers, cellulose triacetate, glasses, and optical materials. Exemplary polymers include: polypropylene, ethylene propylene copolymers, ethylene propylene butene terpolymers, propylene butene copolymers, blends of polypropylene and propylene copolymers, polyetheretherketone, polyimide, polyamide, polysulfone, polyphenylene sulphide, polyamideimide, polyethersulphone, polyetherimide, polyphenylsulphone, polycarbonate, polyacrylate, including polymethacrylate homopolymers and copolymers, polyester, epoxy-based polymers, polysiloxane.

An example of holographic or optically variable devices can be found in U.S. Pat. No. 5,032,003, and in U.S. Pat. Pub. No. US 2005/0112472 A1. An example of holographic or optically variable materials can be found in U.S. Pat. No. 5,781,316 and U.S. Pat. Pub. No. US 2004/0101982 A1. These references are incorporated by reference.

The optical quality of OVD or OVM means the optical properties, which are measured by the method proposed here, and that relate directly to the "optimum" or "best" values that are attainable based on understanding of the underlying physics. For example, the diffraction efficiency of an OVD or OVM can be measured and compared to the best possible value that is attainable based on the understanding of the underlying physics. The underlying physics in this case might be the "optimum" or "best" values of the period and depth of the grating that is embossed on the surface.

The optical characteristics of OVD or OVM means the optical properties, which are measured by the method proposed here, and that relate directly to the "desired" or "target" values that are attainable based on specific applications or customer requirements. For example, the diffraction efficiency of an OVD or OVM can be measured and compared to the "desired" or "target" values that a customer requires. This information could be used to control a manufacturing process to produce the desired OVD or OVM or to set quality standards.

The visual appearance of OVD or OVM means the optical properties, which are measured by the method proposed here, and that relate directly to the "perceived visual effect" that is desired by a customer, artwork designer, or process control person. For example, the diffraction efficiency of an OVD or OVM that is found to be desirable due to its "perceived visual effect" can be controlled in the manufacturing process. In addition, an artwork designer could produce original artwork, which utilizes this desirable "perceived visual effect".

Assessment of the optical quality of holographic films and artwork is currently entirely subjective. A need exists for practical methods of making objective quantitative assessments of quality of optically variable devices and optically variable media. Such methods must produce repeatable results and provide standards by which media can be reliably evaluated. Such methods would be useful in assessing new designs of OVD and OVM, provide standard for assessing the quality of purchased devices and for quality control in the production of OVD and OVM. The application of these methods would therefore result in (a) reduced manufacturing costs (b) improved film quality and consistency and (c) an improved capability to match customer requirements.

SUMMARY OF THE INVENTION

In an exemplary embodiment, a method of evaluating an optically variable device ("OVD") or optically variable media ("OVM") is disclosed. The method includes the steps of applying light of a single wavelength from a calibrated light source to the OVD or OVM; measuring the light diffracted by the OVD or OVM with an integrating sphere; measuring the total incident light on the OVD or OVM; and calculating a diffraction efficiency for the OVD or OVM at the single wavelength based on the measurement of light diffracted and the measurement of total incident light. In a further embodiment, the method includes performing the above-stated steps for a plurality of wavelengths. In a further embodiment, the calculated diffraction efficiencies are corrected to account for the wavelength dependent response of the human eye. In a further embodiment, the measured diffraction efficiencies are compared with model data for OVD or OVM having known diffraction grating characteristics to estimate the diffraction grating characteristics of the OVD or OVM under test. In a further embodiment, target OVD or OVM are selected manually through human perception. These and further embodiments are described in detail below.

DESCRIPTION OF THE PREFERRED EMBODIMENT OF THE INVENTION

Without further elaboration, the foregoing will so fully illustrate this invention that others may, by applying current or future knowledge, readily adopt the same for use under various conditions of service.

Figure 1:
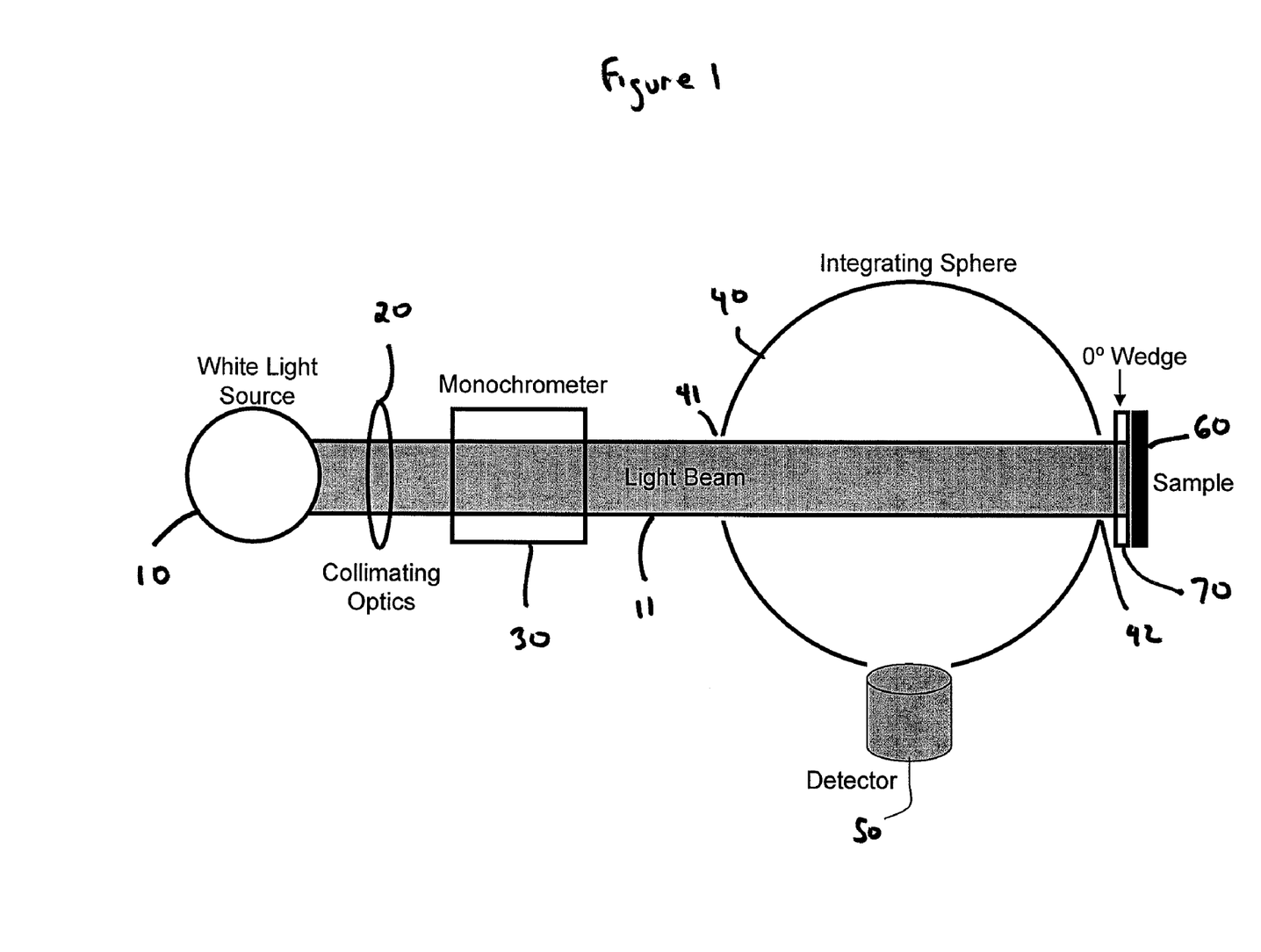
FIG. 1 is a block diagram of an exemplary system for measuring optically variable devices and optically variable media.

With reference to FIG. 1, an exemplary system for measuring OVD and OVM includes the following elements: a white light source 10, collimating optics 20, a monochrometer 30, an integrating sphere 40 and a detector 50. In the embodiment shown in FIG. 1, a sample OVD or OVM 60 is placed at the edge the integrating sphere 50. A white light source 10 produces a light beam 11 that is collimated by collimating optics 20 and directed to a monochrometer 30. The monochrometer filters the light beam 11 from the white light source 10 so that the light beam 11 is limited to a single wavelength, or a narrow wavelength band. Typically, the monochrometer 30 is controllable by a computer (not shown) that can automatically select any of a variety of light wavelengths. The single wavelength beam is directed through a light wedge 70, behind which is the sample 60. The sample both reflects and diffracts the light beam 11. If the light wedge 70 is a 0 degree light wedge, the integrating sphere 40 collects the majority of light that is refracted from the sample, but very little of the light that is directly reflected from the sample as the sphere has an opening 41 through which light that is returned along the axis through which the light beam 11 was introduced exits without illuminating the integrating sphere. A detector 50 measures the total amount of light that is collected by the integrating sphere 40. Where the light wedge is a 0 degree wedge, this measurement is essentially all of the light that is diffracted by the sample, 60 with none of the light that is directly reflected by the sample being measured. In order to assess the amount of light directly reflected from the sample 60, a light wedge 70 with an angle greater than 0 degrees is placed in front of the sample 60. This causes any directly reflected light to not exit through the opening 41 in the integrating sphere and to illuminate the sphere and be thereby measured by the detector 50. In this manner, measurements of nearly all light reflected and diffracted by the sample and of light that is just diffracted by the sample can be made at a plurality of wavelengths.

One embodiment of the method consists of using a spectrophotometer (for example an embodiment employing Cary 300 UV-Visible Spectrophotometer manufactured by Varian is described in detail below) that has an integrating sphere. As described above, the light that is incident on the film comes from a white light source and through collimating optics and a monochrometer and is continuously measured and calibrated by the electronics of the spectrophotometer.

To measure incident light from the light beam 11 that illuminates the sample 60, a diffuse reflectance standard is placed at the aperture 42 of the integrating sphere 40, where the films or OVDs are placed that will be measured. The spectra of this standard is measured and allows calibration of the collection efficiency of the integrating sphere 40. One embodiment of the method consists of using a Spectralon standard, which is 99+% reflective over all wavelengths, which allows the calibration of the integrating sphere efficiency (which is near 50%) versus the wavelength of the light. This calibration factor is then applied versus wavelength to calculate the true corrected diffraction efficiencies and reflectivities. These corrected figures represent objective measures of optical characteristics which can be used to assess optical quality as described further herein.

Example Using Varian Spectrophometer

The Varian Cary 300 is a precision UV-Visible Spectrophotometer that has a wavelength range between 200 to 800 nm, wavelength accuracy of ±0.2 nm, and a spectral slit width from 0.2 to 4 nm in 0.1 nm steps. It has a calibrated light source with a grating monochromer, which allows the wavelength of the light to be scanned one wavelength a time onto an optical detector. The Spectrophotometer can be used to measure transmission or reflection spectra. For reflection, the calibrated white light source is directed onto a grating monochromer, which selects a particular wavelength of light. That wavelength of light is then directed onto the sample. The light reflected from the sample is then collected and directed to the calibrated optical detector. The next wavelength of light is then selected by the monochrometer and the process is repeated until all of the desired wavelengths of light have been measured. A plot of the percent of light reflected versus wavelength can be produced from this data.

For metalized holographic films, it is desirable to measure the percentage of visible light that is diffracted by the holographic gratings versus the wavelength the light. The Labsphere DRA-CA-30I Diffuse Reflectance accessory for the Cary 300 allows this measurement. The DRA-CA-301 consists of an integrating sphere, which is able to collect any light that is scattered by the film. To do this, the accessory is first placed in the Cary 300 sample compartment. The holographic film sample is then placed at the reflectance port with either the metalized or unmetalized side toward the integrating sphere, depending on which side is to be characterized. The Cary 300 is then scanned typically over a wavelength range of 400 nm to 800 nm, which includes the visible range of light. The integrating sphere collects all of the scattered light but not the direct reflected (specular) light, which is directly reflected back out of the transmittance port. A plot of the percent of the scattered light versus wavelength is then produced from this data. There are two contributions to this scattered light. One is from the holographic grating and the other is from any other surface roughness or inhomogeneities on the film. If the surface roughness and inhomogeneities are small compared to the grating, then most of the light collected will be from the grating. This allows a direct measurement of the holographic film total diffraction efficiency.

The total light reflected from the film can also be measured with this attachment. An 8° wedge sample holder is placed at the reflectance port. This tilts the film sample enough so that the directly reflected light does not exit the integrating sphere but is captured in the sphere. The wavelength is scanned as before. This allows measurement of all of the light reflected by the film over all wavelengths for calibration purposes.

Experimental Data

The results of these measurements can also be compared to those from an appropriate theoretical model, which can predict the optical characteristics of the sample based on the grating period and depth. Physical measurements of the grating period, depth and shape can be made with an Atomic Force Microscope (AFM), Scanning Electron Microscope (SEM), or other suitable methods. These results can then be correlated, using the theory, to the results of the spectrophotometer measurements.

In addition, theoretical models of diffraction efficiency from gratings can be fit to the results of the spectrophotometer measurements. Using these results, the grating period, depth and shape can be determined directly from the spectrophotometer measurements. This technique allows direct measurement of the grating characteristics without the use of an Atomic Force Microscope (AFM) or Scanning Electron Microscope (SEM). These characteristics are fundamentally important in the physics of grating diffraction.

Once the correlation is made, the spectrophotometer measurements show not only how much light is reflected or diffracted at each wavelength but also indicate the depth and period of the grating. With this information, the depth and/or period of the grating can then be modified to allow the optical characteristics of the gratings or holograms to be optimized for diffraction efficiency, reflectivity, color content, angle of diffraction, diffraction orders, etc. In addition, this method can be used to monitor production processes, to set standards/specifications for quality or acceptance of artwork or products, or for statistical process control. This information can be used to determine the optical quality (OQ), the optical characteristics (OC), or the visual appearance (VA) of OVD or OVM. In addition, this method has the advantage over SEM and especially AFM that it can utilize a relatively larger area of the sample (typically 0.05 square inches or larger) which is more representative of the OQ, OC and VA.

In addition, this method can be used to simulate what a person sees, (the visual appearance (VA) of OVD or OVM by evaluating the light reflected and diffracted relative to the known response of the human eye. A human eye is more sensitive to certain wavelength, such as 555 nm and less sensitive to other wavelengths, such as 470 nm or 670 nm. Weighting the spectral diffraction response of OVD as measured by the integrating sphere by the spectral sensitivity of a human eye gives a more accurate description of the visual appearance. Furthermore, additional weighting can account for the spectral emission of a particular light source. This gives a more accurate description of the visual appearance under specific lighting conditions. The data relating to response of the human eye and how to apply this data is well known to those skilled in the art. This allows the development of an objective standard for comparison of the human perceived brightness, uniformity, and color content of gratings and holograms. Furthermore, criteria can be identified and quantified that establish the specific optical characteristics of a product that results in customers finding it desirable. These characteristics can form a "fingerprint" of desirable types of holographic films. These visual characteristics can be identified and modified to produce a desired fingerprint. For example, the optimum grating depth, period, shape, embossing surface thickness or composition, dot overlap or gap, statistical variation of all these parameters, etc. can all be specified so that a product is well defined.

The relationship between perceived optical quality and measured diffraction efficiency and physical characteristics of optically variable device can be seen in the following example.

Figure 2:
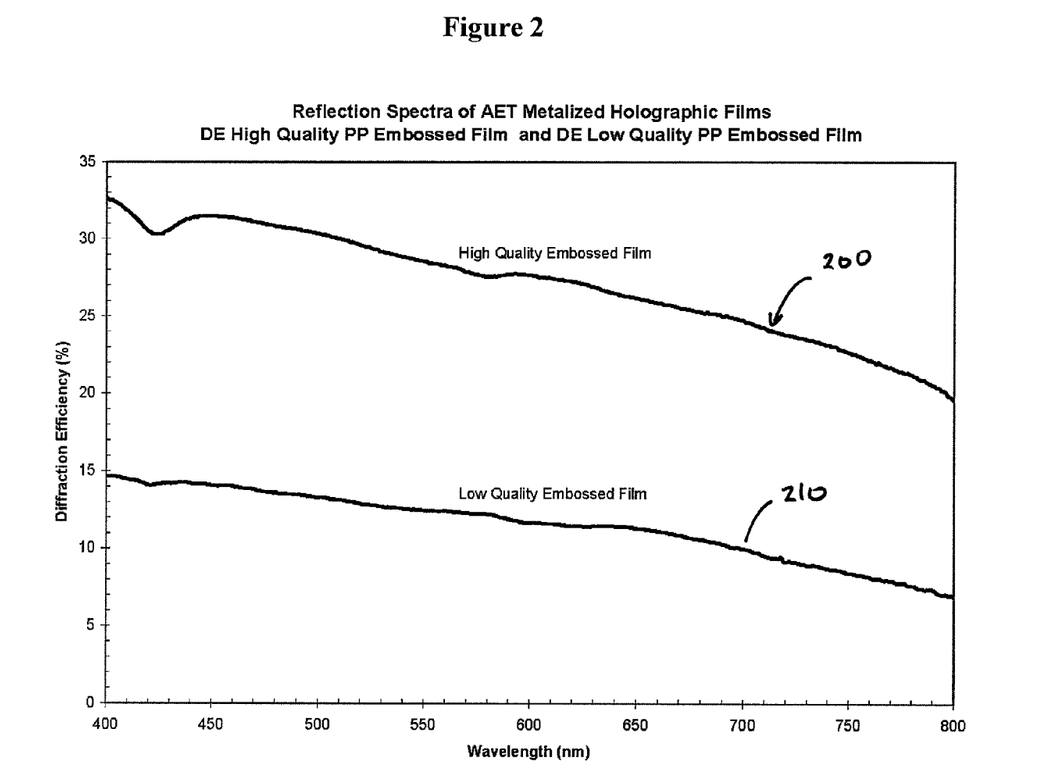
FIG. 2 is a graph of measured diffraction spectra of two holographic films.

One use of the method described above is to demonstrate that the visual brightness of an embossed holographic film is measurable using spectroscopy and that this measurement correlates with what people perceive to be bright films. In an experiment which employed the above-described embodiment, the diffuse reflection spectra of two samples of embossed films with an identical surface relief pattern were measured versus the wavelength of light. One sample was perceived as high brightness and the second was seen as low brightness. FIG. 2 shows the uncorrected data. The curve for the high brightness film 200 is over twice as bright as the curve for the low brightness film 210 over all wavelengths. The spectra also show that both films are also much brighter at shorter wavelengths (blue) that they are at longer wavelengths (red). Therefore, it is possible to not only measure the perceived brightness of a holographic film but to also quantify its brightness versus wavelength.

Figure 3:
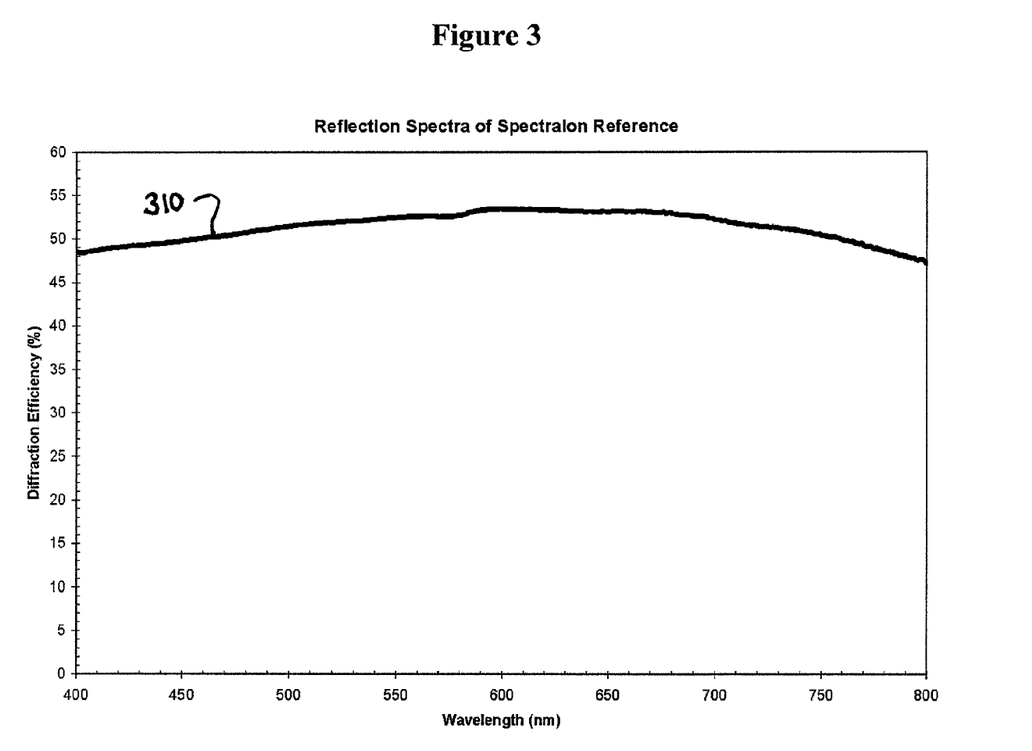
FIG. 3 is a graph of reflection spectra for a Spectralon reference.

The spectra in FIG. 2 are uncalibrated. They are the raw data that comes from the spectrophotometer. This data must be calibrated for the reflectance of the integrating sphere. The best way to do this is to run spectra of a known high reflectance material, which can serve as a baseline measurement. FIG. 3 shows a curve 310 of the diffuse reflectance spectra of a Spectralon reference obtained from Labsphere. The reference is known to have a reflectivity of greater than 99% over all of the visible wavelengths. By dividing the spectra 200, 210 in FIG. 2 by this spectrum 310 in FIG. 3 the corrected diffraction efficiency can be obtained.

Figure 4:
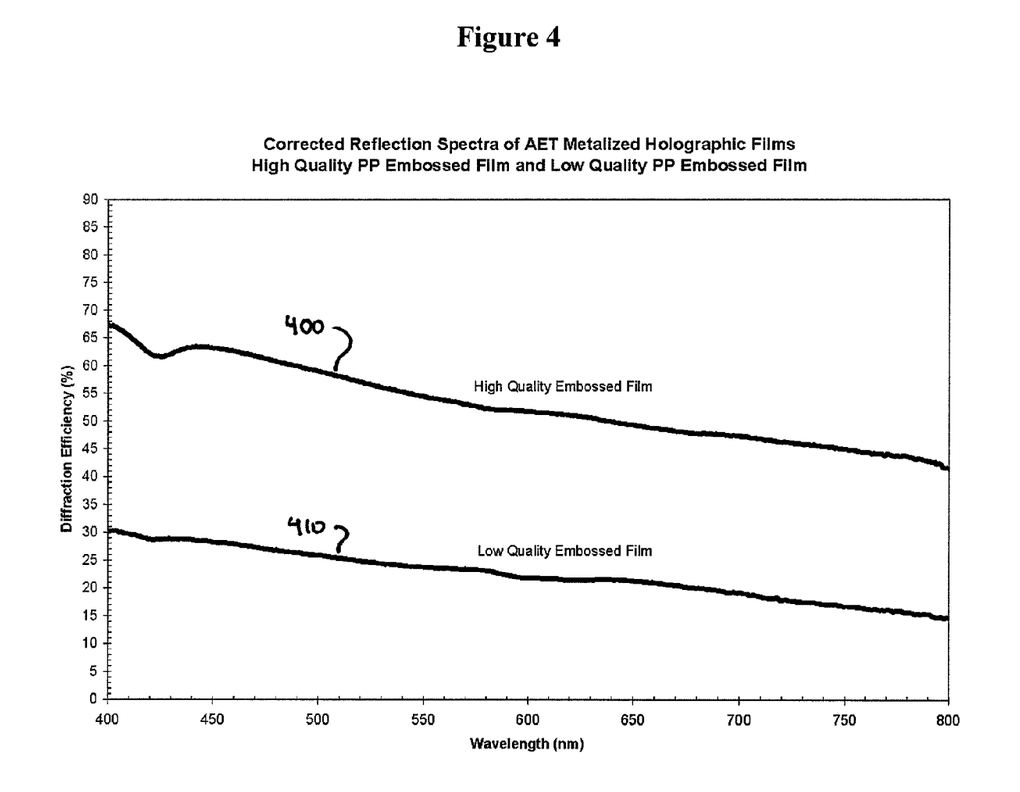
FIG. 4 is a corrected graph of measured diffraction spectra of two holographic films.

FIG. 4 is the corrected spectra of FIG. 2 and shows the true diffraction efficiency for each of these films. FIG. 4 shows that the curve for the high quality film 400 has a diffraction efficiency of about 67% in blue light (400 nm wavelength), while the curve for low quality film 410 has only about 31% diffraction efficiency. Also, the high quality film has a diffraction efficiency of about 42% in red light (700 nm wavelength) while the low quality film has only about 17% diffraction efficiency. Based on the objective measured data overall, the high quality film is more than twice as bright as the low quality film.

Relationship Between Grating Depth and Diffraction Efficiency

The diffraction efficiency theory of gratings can be used in conjunction with spectroscopic measurements using the integrating sphere described herein to not only characterize the holographic films brightness but to also determine physical characteristics of the films such as grating depths and periods. There are a large number of theoretical treatments of the diffraction of gratings, which are well known to those skilled in the art. These range from simple diffraction theory to electrodynamics calculations to complex computer simulations using advanced numerical techniques. Predicted diffraction efficiency can also be calculated by using a Fourier transform, a 2D Fourier transform, a Fourier transform calculated using numerical methods on a computer, a 2D Fourier transform calculated using numerical methods on a computer, or a power spectrum distribution model calculated using numerical methods on a computer. All of these theories have limitations and may involve theoretical approximations. However, it is possible to get valuable and accurate grating information from even simple diffraction theory, as is shown below.

For a diffraction grating, the direction of the diffracted light is given by grating equation $$m\lambda = d(\sin \alpha + \sin \beta)$$

where m is the order of the diffraction, $\lambda$ is the wavelength of the light, d is the period of the grating, $\alpha$ is the angle of incidence of the light onto the grating relative to the normal to the surface and $\beta$ is the angle that the light is diffracted by the grating relative to the normal to the surface. And if the light is incident directly from above as in this case then $$\alpha = 0$$

and $$\sin \alpha = 0$$

the grating equation then becomes $$m\lambda = d \sin \beta$$

then the angles that the diffraction orders occur at are $$\beta_m = \sin^{-1}\left(\frac{m\lambda}{d}\right)$$

where the diffraction orders are m=0, ±1, ±2, ±3, etc.
The diffraction efficiency ($\eta$) for m=1 is given by $$\eta = \sin^2\left(\frac{\pi \cdot a}{\lambda \cos\theta_0}\right)$$

Where $\theta_0$ is the Bragg angle, which is the angle of maximum diffraction efficiency for a particular wavelength of light and depending on the grating period.

In embodiments using an integrating sphere to collect the diffracted light where the incident light is approximately normal to the surface, an approximation to the Bragg angle that best represents the detection method can be used. In this embodiment, a Littrow mounting approximation can be used. This approximation is similar to the so called flat-field spectrometer, which has the grating in a mount where the angle of incidence is constant and the wavelength scan is performed by using different diffraction angles. The equation for $\cos \theta_0$, based on the Littrow mounting, is given below.

$$\cos\theta_0 = \sqrt{1 - \left(\frac{\lambda}{2d}\right)^2}$$

By substitution, the equation for the diffraction efficiency ($\eta$) is $$\eta = \sin^2\left(\frac{\pi \cdot a}{\lambda\sqrt{1 - \left(\frac{\lambda}{2d}\right)^2}}\right)$$

Figure 5:
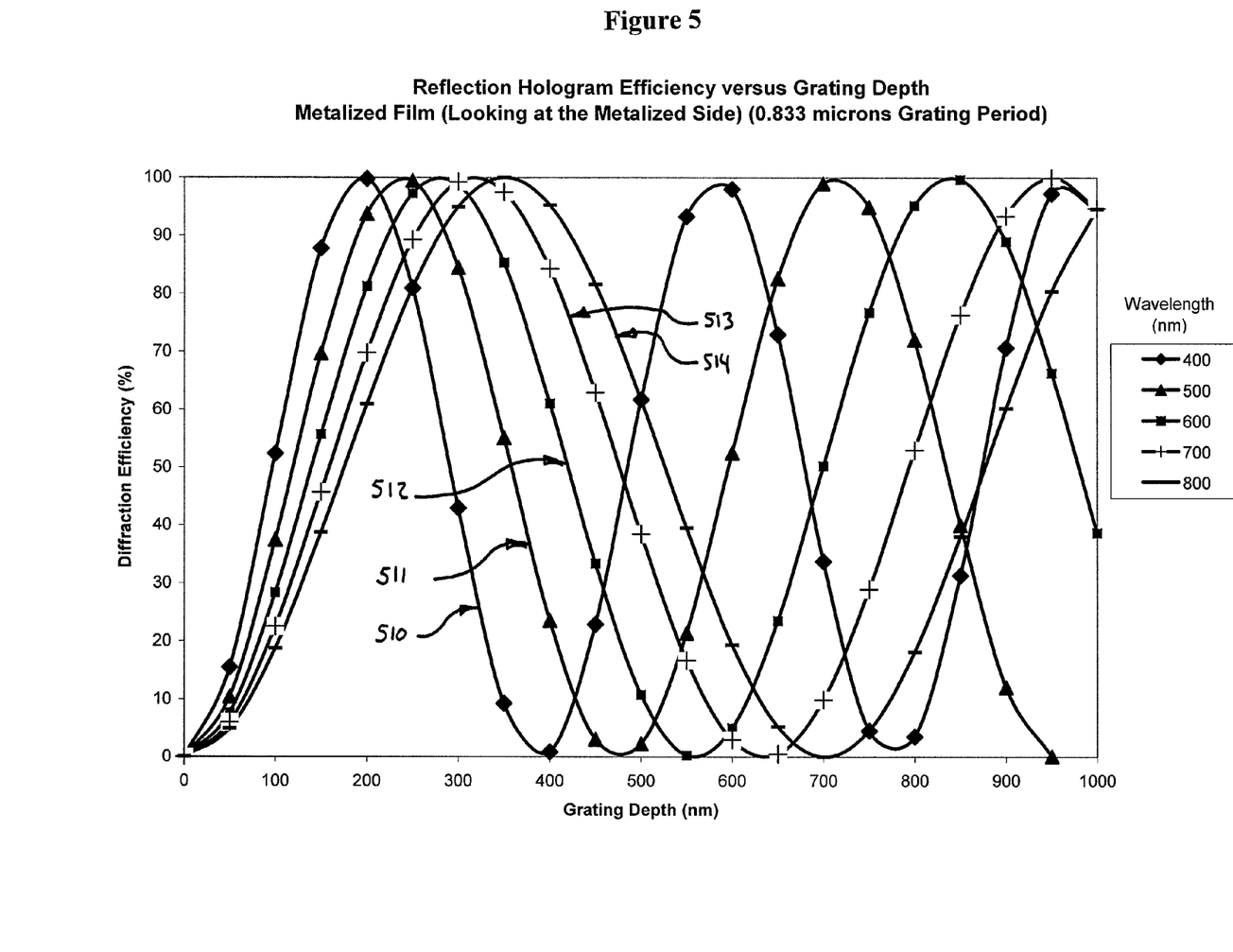
FIG. 5 is graph of predicted hologram efficiency versus grating depth.

FIG. 5, shows what this theory predicts for the diffraction efficiency of a grating with a period of 0.833 µm, coated with a perfectly reflecting metal, versus the grating depth for wavelengths of light between 400 nm and 800 nm. This shows that, even for a perfectly reflecting metal; all wavelengths of light cannot be diffracted at 100% efficiency for a particular depth of grating. The optimum grating depth for blue light (400 nm wavelength) shown by curve 510 is about 200 nm while the optimum depth for red light (800 nm wavelength) shown by curve 514 is about 370 nm. At a depth of about 260 nm, then all wavelengths of light will be diffracted at about 80% or better. Curves for other wavelengths are as follows: 500 nm (curve 511), 600 nm (curve 512) and 700 nm (curve 513) The theory demonstrates that choosing an optimum depth is important to achieve the optimum film diffraction efficiency.

To demonstrate the predictions of the theory, an evaluation was made with six scientific grade gratings form Optometrics. The gratings had the same grating period of 0.833 µm and grating depths ranging from 123.6 nm to 400 µm. These gratings are not ideal because they are replicated blazed gratings and not holographic sinusoidal gratings. However, they could be obtained with a number of grating depths, which are not easily available for scientific grade holographic gratings. Table 1 below gives the data for all of these gratings.

TABLE 1

Data for gratings purchased from Optometrics.

| Optometrics Grating | Grating Period (microns) | Grating Depth (nm) | Blaze Angle (deg) | Facet Size (nm) | Blaze Wavelength (nm) |
|---|---|---|---|---|---|
| 3-8125 | 0.833 | 123.6 | 8.63 | 823.9 | 250 |
| 3-8130 | 0.833 | 147.5 | 10.37 | 819.7 | 300 |
| 3-8140 | 0.833 | 194.2 | 13.89 | 809.0 | 400 |
| 3-8150 | 0.833 | 238.5 | 17.46 | 794.9 | 500 |
| 3-8175 | 0.833 | 334.9 | 26.74 | 744.2 | 750 |
| 3-8110 | 0.833 | 400.0 | 36.87 | 666.7 | 1000 |

Diffraction efficiencies were measured using the embodiment described above, with the Cary 300 and the integrating sphere attachment. The measurements were corrected as described above. The diffraction efficiency was then averaged over all wavelengths for each spectrum to obtain the total diffracted light efficiency for each grating depth. A plurality of measurements were made for each grating while changing the orientation of the grating, to get statistical information and to see if there was any effect due to grating orientation.

Figure 6:
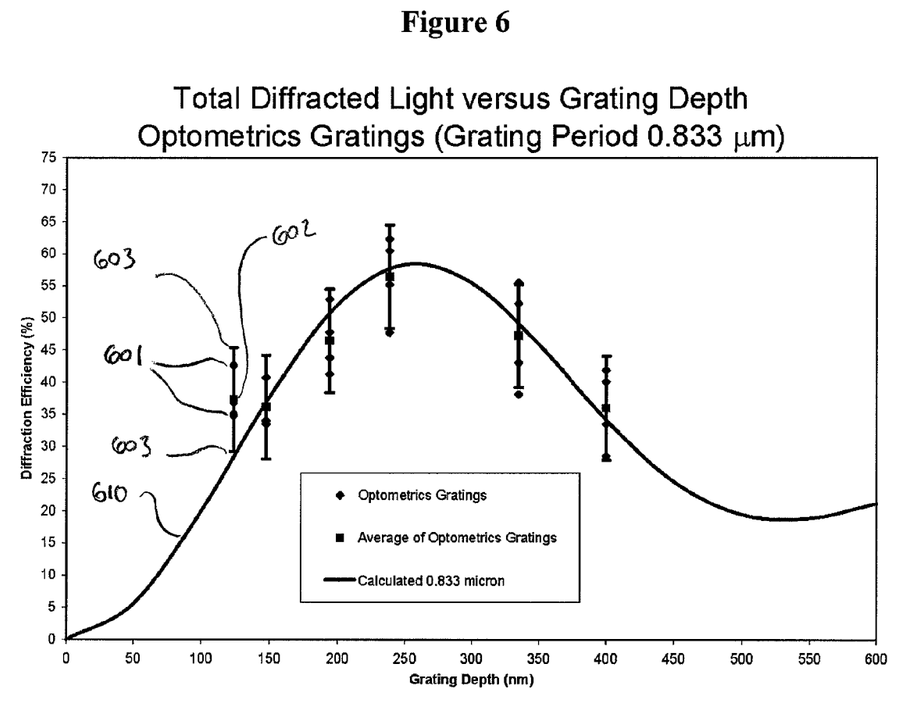
FIG. 6 is a graph of measured and predicted hologram efficiency versus grating depth.

FIG. 6 shows the total diffraction efficiency over all wavelengths versus the grating depth. The measured data is shown as dots 601, the average of the data is shown as squares 602, and the horizontal lines 603 represent ±1σ standard deviation of the data. Note that these designations apply for each data set even though only the leftmost data set is labeled. The predicted efficiency according to the above is plotted theory is the curve line 610 which is corrected for the total reflectivity of the aluminum coating on the gratings. There is a very good fit of the data to the theory. This indicates that the grating theory can predict the optimum grating depth to produce the highest diffraction efficiency for holographic films and also might be used to monitor or control the embossing process, since the grating depth might be correlated to the brightness of the film. In principle, it should be possible to measure the diffraction efficiency of the film according to the embodiments describe herein and then use the theory to determine the depth of the gratings.

Figure 7:
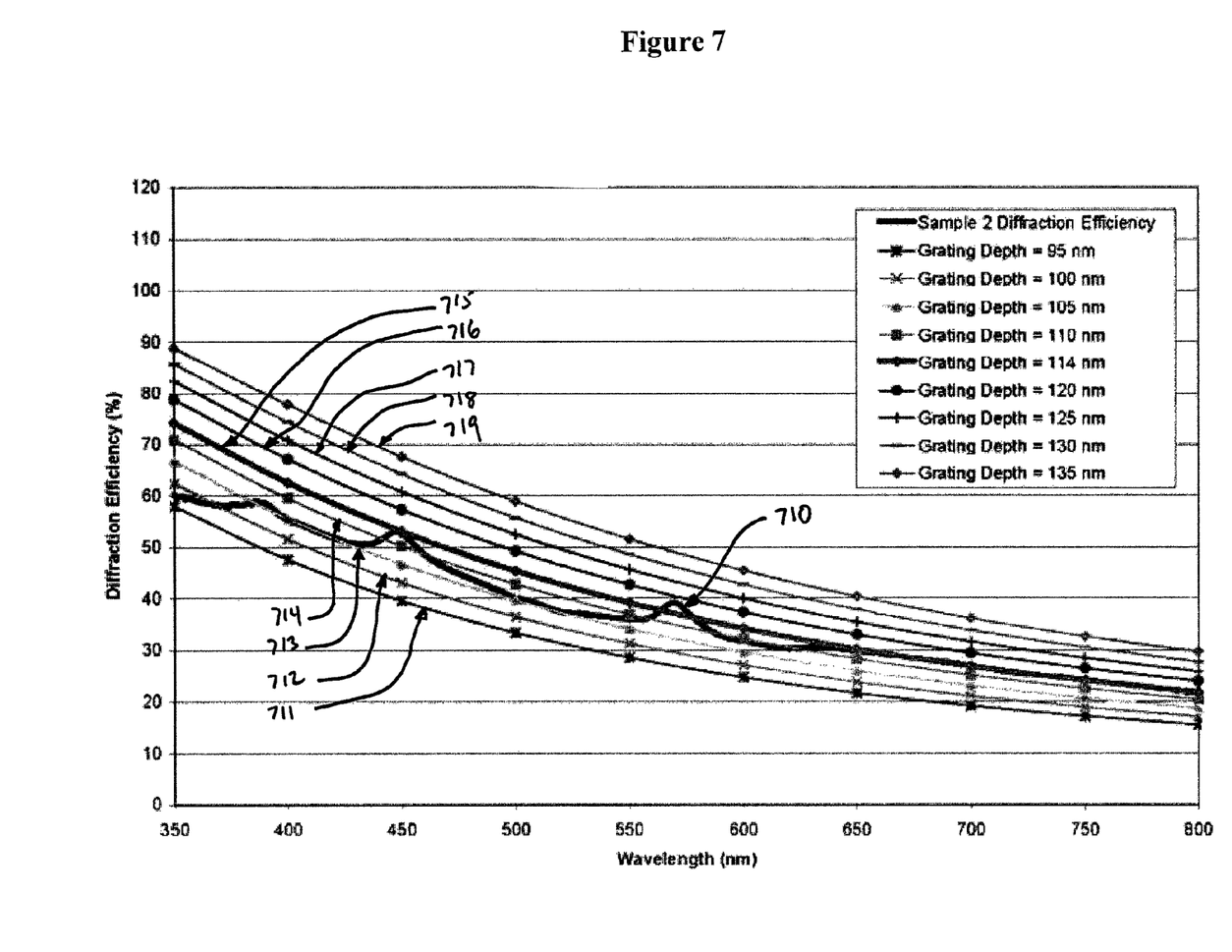
FIG. 7 is a graph of a measured diffraction spectra and theoretical fits versus grating depth.

FIG. 7 shows a curve 710 representing the diffraction efficiency versus the wavelength of light for an embossed film. The data from which this curve was constructed was measured using the embodiment described above with the Varian Cary 300. Using the diffraction theory described above, the diffraction efficiency versus the wavelength of light was calculated for a number of grating depths. The diffraction efficiency curves for various grating depths are as follows: 95 nm (curve 711), 100 nm (curve 712), 105 nm (curve 713), 110 nm (curve 714), 114 nm (curve 715), 120 nm (curve 716), 125 nm (curve 717), 130 nm (curve 718) and 135 nm (curve 719). It is apparent that the best fit between the theory and the measured diffraction efficiency is for a grating depth of 114 nm. Note that curve 710 overlaps the curve 715 for a 114 nm grating from wavelengths above about 650 nm. Grating depths of 110 nm and 120 nm are obviously worse fits to the measured diffraction efficiency. This shows that the average grating depth of the embossed film can be measured using this technique to an accuracy of at least ±5 nm. This is a high precision measurement but it is not the limit of the precision of this technique. Even higher precision measurements are possible using a better Spectrophotometer and more complex theories of diffraction. These types of accuracies are also possible for AFM and SEM but not over the large area (approximately 0.05 square inches) measured with this technique.

Other Embodiments

The spectrophotometer and integrating sphere are the major instruments used in this technique. However, other embodiments could be used to measure similar or complementary information. For example a laser could be used along with a goniometer and would give results for only one wavelength but at many different angles. Other embodiments using lamps, lasers, goniometers, integrating spheres, monochrometers, optical detectors, Charge Coupled Device (CCD) cameras, etc. are possible.

What is claimed is:

1. A method of evaluating an Optically Variable Device (OVD) or Optically Variable Media (OVM), comprising the steps of:
   a) applying light of a single wavelength from a calibrated light source to the OVD or OVM;
   b) measuring light diffracted by the OVD or OVM with an integrating sphere;
   c) measuring total incident light on the OVD or OVM; and
   d) calculating a diffraction efficiency for the OVD or OVM at said single wavelength based on said measurement of light diffracted and said measurement of total incident light.

2. The method of claim 1, further comprising the steps of:
   a) repeating the steps of claim 1 for a plurality of wavelengths;
   b) calculating an efficiency result for said plurality of wavelengths.

3. The method of claim 2, wherein said efficiency result is selected from the group consisting of
   a) an average diffraction efficiency;
   b) a weighted average diffraction efficiency;
   c) an integral diffraction efficiency; and
   d) a weighted integral diffraction efficiency.

4. The method of claim 2, further comprising correcting said efficiency result to account for a wavelength dependent response of a human eye.

5. The method of claim 4, wherein said wavelength dependent response of a human eye comprises red, green and blue components.

6. The method of claim 1, wherein applying said calibrated light is done with a spectrometer.

7. A method of evaluating optical characteristics of an Optical Variable Device (OVD) or Optically Variable Media (OVM), comprising the steps of:
   a) measuring a diffraction efficiency the OVD or OVM for a plurality of wavelengths;
   b) establishing a desired optical characteristic for a particular OVD or OVM design; and
   c) evaluating a plurality of OVDs or OVMs having said particular design by performing step "a" for each one of said plurality and comparing the result of step "a" with said desired optical characteristic.

8. The method of claim 7, wherein said desired optical characteristic is selected from the group consisting of:
   a) diffraction efficiency;
   b) reflectivity;
   c) scatter;
   d) weighted average diffraction efficiency;
   e) weighted average reflectivity;
   f) weighted average scatter; and
   g) color spectra.

9. The method of claim 7, wherein said optical characteristic is established though manually selecting a particular OVD or OVM target through human perception.

10. The method of claim 9, wherein said OVD or OVM target is established through a theoretical model, wherein said theoretical model predicts efficiency over a plurality of wavelengths.

11. The method of claim 7, wherein said measured diffraction efficiency is selected from the group consisting of:
    a) an average diffraction efficiency;
    b) a weighted average diffraction efficiency;
    c) an integral of the diffraction efficiency; and
    d) weighted integral of the diffraction efficiency.

12. The method of claim 7, wherein said diffraction efficiency is calculated by a method selected from the group comprising:
    a) standard diffraction theory;
    b) electrodynamics calculations;
    c) a Fourier transform;
    d) a 2D Fourier transform;
    e) a power spectrum distribution model;
    f) standard diffraction theory calculated using numerical methods on a computer;
    g) electrodynamics calculations calculated using numerical methods on a computer;
    h) a Fourier transform calculated using numerical methods on a computer;
    i) a 2D Fourier transform calculated using numerical methods on a computer; and
    j) a power spectrum distribution model calculated using numerical methods on a computer.

13. The method of claim 7, wherein the OVD or OVM is selected from the group consisting of:
    a) a surface relief hologram;
    b) a reflection hologram;
    c) an absorption hologram;
    d) a transmission hologram;
    e) a polarization hologram;
    f) a phase gratings;
    g) a multi-layer diffractive device;
    h) a multi-layer refractive device;
    i) a random scattered surface;
    j) a random scattered inclusions; and
    k) a random scattered layer.

14. The method of claim 7 where said evaluation is a part of a statistical process control method for the production of OVD or GyM.

15. The method of claim 7 where said evaluation is performed as a part of a real time process control method for the production of OVD or OVM.

16. The method of claim 7 where the evaluation is done on an OVD or OVM substantially made from a polymer.

17. The method of claim 7 where the OVD or OVM is made of a polymer selected from the group consisting of:
 a) polypropylene
 b) ethylene propylene copolymers;
 c) ethylene propylene butene terpolymers;
 d) propylene butene copolymers;
 e) blends of polypropylene and propylene copolymers
 f) polyetheretherketone;
 g) polyimide;
 h) polyamide;
 i) polysulfone;
 j) polyphenylene sulphide;
 k) polyamideimide;
 l) polyethersulphone;
 m) polyetherimide;
 n) polyphenylsulphone;
 o) polycarbonate;
 p) polyacrylate, including polymethacrylate homopolymers and copolymers;
 q) polyester;
 r) epoxy-based polymers; and
 s) polysiloxane.

18. The method of claim 7 where the evaluation is performed on a film selected from the group consisting of
 a) an embossed film;
 b) a transferred holographic image;
 c) an unmetallized film; and
 d) a metallized film.

19. The method of claim 7 wherein said measuring is performed with an integrating sphere.

20. A method for evaluating an Optically Variable Device or Optically Variable Media under test having a grating depth and period, comprising the steps of:
 a) applying light of a single wavelength to the OVD or OVM under test with a calibrated light source;
 b) collecting and measuring light diffracted by said OVD or OVM under test with an integrating sphere;
 c) calculating a wavelength dependent diffraction efficiency of the OVD or OVM under test using said measured diffracted light;
 d) applying light of a single wavelength to the OVD or OVM under test with a calibrated light source;
 e) collecting and measuring light reflected by said OVD or OVM under test with an integrating sphere;
 f) calculating a wavelength dependent reflectivity for the OVD or OVM under test;
 g) Normalizing said diffraction efficiency relative to said reflectivity;
 h) Repeating steps "a"-"g" for a plurality of wavelengths;
 i) selecting an exemplary OVD or OVM target having a known normalized diffraction efficiency; and
 j) Evaluating the OVD or OVM under test by comparing said normalized diffraction efficiency with said known normalized diffraction efficiency of said exemplary OVD or OVM.

21. The method of claim 20, wherein applying said calibrated light is done with a spectrometer.

22. The method of claim 20, wherein said OVD or OVM target is established though manually selecting a particular OVD or OVM target through human perception.

23. The method of claim 20, wherein said OVD or OVM target is established through a theoretical model, wherein said theoretical model predicts efficiency over a plurality of wavelengths.

24. The method of claim 23 wherein said theoretical model predicts a curve based on one of the group consisting of:
 a) standard diffraction theory;
 b) electrodynamics calculations;
 c) a Fourier transform;
 d) a 2D Fourier transform;
 e) a power spectrum distribution model;
 f) standard diffraction theory calculated using numerical methods on a computer;
 g) electrodynamics calculations calculated using numerical methods on a computer;
 h) a Fourier transform calculated using numerical methods on a computer;
 i) a 2D Fourier transform calculated using numerical methods on a computer; and
 j) a power spectrum distribution model calculated using numerical methods on a computer.

25. The method of claim 20 further comprising the step of:
 determining for the OVD or OVM under test any one of the group consisting of
 a) grating depth;
 b) grating period; and
 c) grating shape
by comparing said normalized diffraction efficiency to a theoretical model target and fitting said theoretical model to said normalized diffraction efficiency over a plurality of wavelengths.

26. The method of claim 20, wherein the OVD or OVM is selected from the group consisting of:
 a) a surface relief hologram;
 b) a reflection hologram;
 c) an absorption hologram;
 d) a transmission hologram;
 e) a polarization hologram;
 f) a phase gratings;
 g) a multi-layer diffractive device;
 h) a multi-layer refractive device;
 i) a random scattered surface;
 j) a random scattered inclusions; and
 k) a random scattered layer.

27. The method of claim 20 wherein the OVD or OVM is substantially made from a polymer.

28. The method of claim 20 wherein the OVD or OVM is made of a polymer selected from the group consisting of
 a) polypropylene
 b) ethylene propylene copolymers;
 c) ethylene propylene butene terpolymers;
 d) propylene butene copolymers;
 e) blends of polypropylene and propylene copolymers
 f) polyetheretherketone;
 g) polyimide;
 h) polyamide;
 i) polysulfone;
 j) polyphenylene sulphide;
 k) polyamideimide;
 l) polyethersulphone;
 m) polyetherimide;
 n) polyphenylsulphone;
 o) polycarbonate;
 p) polyacrylate, including polymethacrylate homopolymers and copolymers;
 q) polyester;
 r) epoxy-based polymers; and
 s) polysiloxane.

29. The method of claim 20 where the OVD or OVM comprises a film selected from the group consisting of
 a) an embossed film;
 b) a transferred holographic image
 c) an unmetalized film; and
 d) a metalized film.

* * * * *